United States Patent
Szeles

(10) Patent No.: US 9,821,153 B2
(45) Date of Patent: Nov. 21, 2017

(54) PUNCTUAL STIMULATION DEVICE

(76) Inventor: Josef Constantin Szeles, Vienna (AT)

(*) Notice: Subject to any disclaimer, the term of this patent is extended or adjusted under 35 U.S.C. 154(b) by 172 days.

(21) Appl. No.: 14/006,331

(22) PCT Filed: Mar. 21, 2012

(86) PCT No.: PCT/IB2012/000559
§ 371 (c)(1),
(2), (4) Date: Dec. 2, 2013

(87) PCT Pub. No.: WO2012/127306
PCT Pub. Date: Sep. 27, 2012

(65) Prior Publication Data
US 2014/0081368 A1   Mar. 20, 2014

(30) Foreign Application Priority Data

Mar. 23, 2011 (AT) ................................. GM168/2011

(51) Int. Cl.
*A61N 1/00* (2006.01)
*A61N 1/04* (2006.01)
(Continued)

(52) U.S. Cl.
CPC .......... *A61N 1/0456* (2013.01); *A61H 39/002* (2013.01); *A61N 1/0526* (2013.01);
(Continued)

(58) Field of Classification Search
CPC .............. A61N 1/0456; A61N 1/36014; A61N 1/36032
(Continued)

(56) References Cited

U.S. PATENT DOCUMENTS 7,336,993 B1   2/2008 Szeles
2007/0250145 A1* 10/2007 Kraus .................. A61H 39/002
607/136
(Continued)

FOREIGN PATENT DOCUMENTS

DE   10 2005 003735 A1   7/2006
WO       01/35897 A1   5/2001
(Continued)

OTHER PUBLICATIONS

Sator-Katzenschlager Sabine M et al: "P-Stim auricular electroacupuncture Stimulation device for pain relief", in: Expert Review of Medical Devices, Future Drugs Ltd., London, GB, vol. 4, No. 1, Jan. 1, 2007, pp. 23-32.

*Primary Examiner* — Amanda Patton
*Assistant Examiner* — Philip C Edwards
(74) *Attorney, Agent, or Firm* — Agris & Von Natzmer, LLP; Joyce Von Natzmer

(57) ABSTRACT

The invention relates to a device for the punctual stimulation of endings, located in the region of the ears, of nerves leading to brain stem nuclei, and device (1) having a battery-powered therapeutic current generator (3), which is arranged in a housing (2) to be worn in the ear region and is provided with an electronic circuit that forms a low-frequency therapeutic current, and said device also having at least one flexible line (5) proceeding from the therapeutic current generator (3) for connecting to an electrode to be positioned at a nerve ending and having a base electrode (7), which is likewise connected to the therapeutic current generator and by means of which the therapeutic circuit leading across the former electrode is closed, wherein the device (1), at least by means of an external part of said device (1), can be adapted to the shape of the body point of patient intended (Continued)

for the positioning of the device due to a mechanically pliable structure.

34 Claims, 4 Drawing Sheets

(51) Int. Cl.
| | |
|---|---|
| *A61H 39/00* | (2006.01) |
| *A61N 1/05* | (2006.01) |
| *A61N 1/36* | (2006.01) |
| *H05K 1/02* | (2006.01) |
| *H05K 1/11* | (2006.01) |
| *H05K 5/00* | (2006.01) |
| *H04R 25/00* | (2006.01) |

(52) U.S. Cl.
CPC ..... *A61N 1/36014* (2013.01); *A61N 1/36017* (2013.01); *H05K 1/028* (2013.01); *H05K 1/118* (2013.01); *H05K 5/0095* (2013.01); *A61H 2205/027* (2013.01); *A61H 2230/065* (2013.01); *A61N 1/0541* (2013.01); *H04R 25/65* (2013.01)

(58) Field of Classification Search
USPC .......................................... 607/136, 137, 139
See application file for complete search history.

(56) References Cited

U.S. PATENT DOCUMENTS

| | | | |
|---|---|---|---|
| 2010/0168822 A1* | 7/2010 | Szeles | A61H 39/002 607/72 |
| 2012/0095527 A1* | 4/2012 | Vardi | A61N 1/36032 607/57 |
| 2012/0226333 A1 | 9/2012 | Szeles | |

FOREIGN PATENT DOCUMENTS

| | | |
|---|---|---|
| WO | 2009/154458 A2 | 12/2009 |
| WO | 2011/030210 A1 | 3/2011 |

* cited by examiner

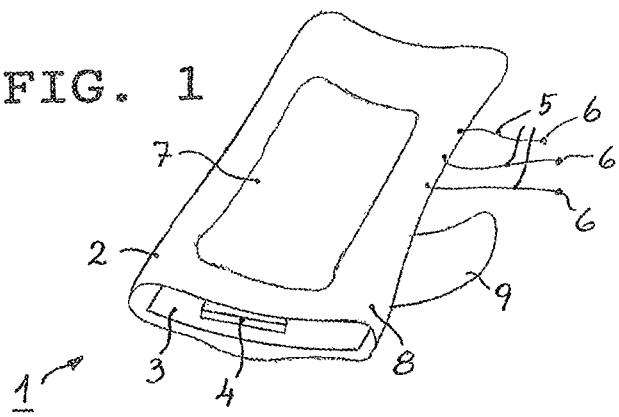
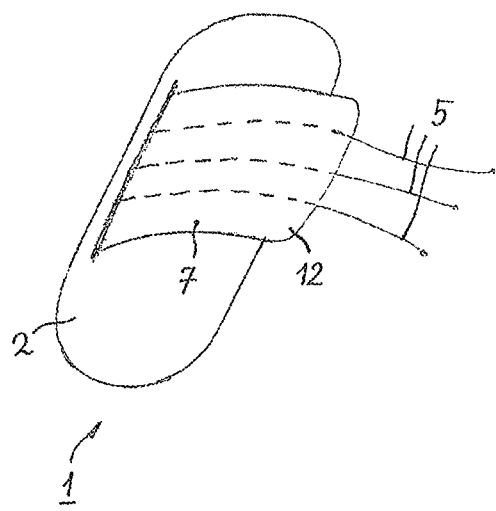
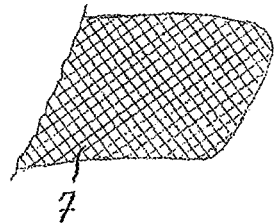

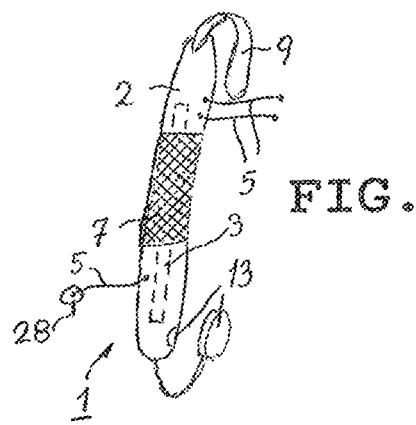
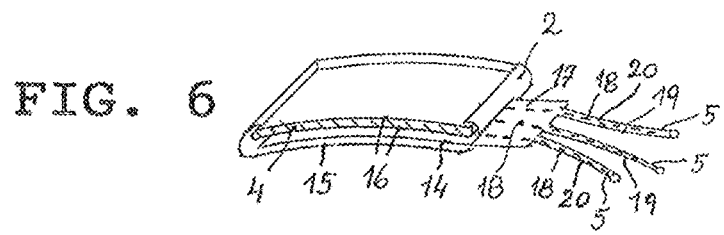
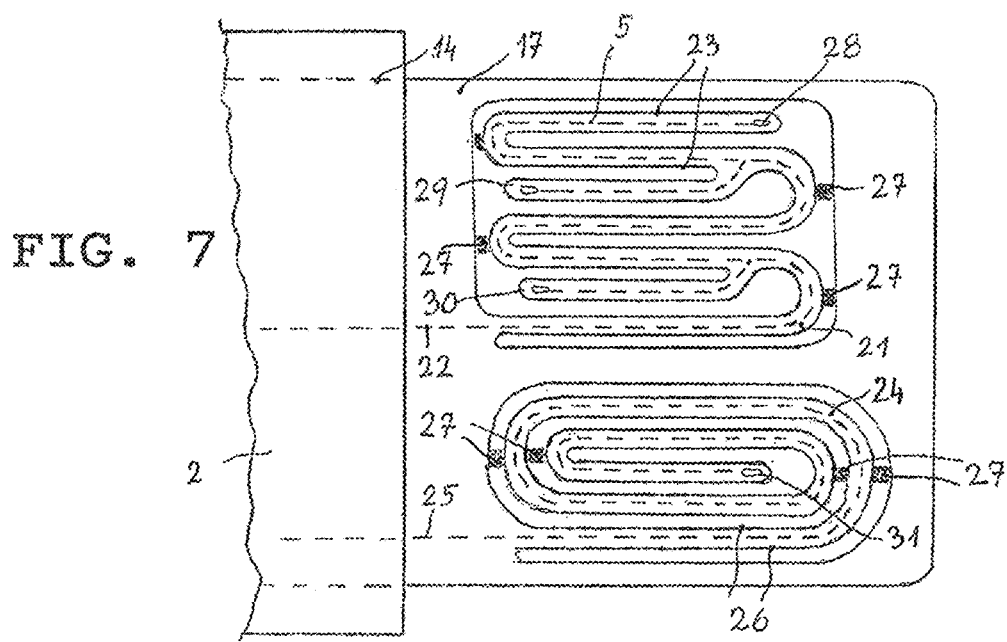

PUNCTUAL STIMULATION DEVICE

CROSS REFERENCE TO RELATED APPLICATIONS

This is the U.S. national of International application PCT/IB2012/000559, filed Mar. 21, 2012 designating the United States and claiming priority to Austrian application AT GM 168/2011, filed Mar. 23, 2011.

The invention relates to a device for punctual stimulation of endings of nerves that are in the region of the ears and that lead to brain stem nuclei, which device has a battery-powered therapeutic current generator that is arranged in a housing to be worn in the region of the ear and that is provided with an electronic circuit that forms a low-frequency therapeutic current, and which device further has at least one flexible cord proceeding from the therapeutic current generator for connecting to an electrode to be positioned on a nerve ending and further has a base electrode, also connected to the therapeutic current generator, via which the therapeutic current circuit leading across the aforesaid electrode is closed.

For good effectiveness of a stimulation therapy that is to be performed over extended periods with a device of the aforesaid type, it is very important to have a good seat for such a device on the body of a patient to be treated. It is now an object of the invention to create an embodiment of a device of the aforesaid type, which device, when attached to a patient, may find a good seat in a simple manner and which device with respect to the seat is somewhat resistant to interfering influences, such as e.g. personal hygiene measures in wet areas. In addition, to the extent possible no obviously visible retention elements should be necessary and it should be possible to realize the embodiment to be created with little complexity.

The inventively embodied device of the aforesaid type is characterized in that due to a mechanically pliable structure the device, or at least an exterior portion of this device, may be adapted to the shape of the body part of a patient provided for positioning it. The aforesaid objective may be attained using this embodiment. When attaching the device to a patient, the device may easily positioned at the provided body part due to the mechanically pliable structure; the positioning on the body counteracts undesired lifting from the body and undesired displacement on the body due to the effects of external forces that may occur during personal hygiene measures. For many applications, it is advantageous to provide a flat base electrode that is embodied mechanically pliable and which is provided for placing on a skin area located in the ear region of a patient. The base electrode forms an exteriorly disposed part of the device and may also alone realize a mechanically pliable part. Over an extended period, good positioning of the base electrode results in uniform conditions in the loop of the therapeutic current. A structurally simple embodiment of the inventive device, which embodiment permits the base electrode to adapt well to the provided body area, is characterized in that the base electrode of the device disposed in the therapeutic circuit is embodied flat and flexible and may be arranged movable in a fan-like manner on the housing of the device. In the context of adapting well and for good electrical contacting it is also advantageous when it is provided that the base electrode has electrically conducting strips or threads that preferably run in a grid-like or net-like manner.

For the seat of the housing of the device on the body part provided for arranging the device, it is advantageous if it is provided that the base electrode is embodied flat and flexible and the wall of the housing of the device is embodied to be flexible, at least on the side on which the flat base electrode is arranged. It is further advantageous if a flat base electrode is arranged positioned against the flexibly embodied wall of the housing. The base electrode may be positioned connected to the flexibly embodied wall of the housing of the device or may be positioned against this wall but not connected thereto.

Another advantageous embodiment of the inventive device is characterized in that the base electrode is a needle electrode that is connected to the therapeutic current generator via a flexible cord. In this way it is possible to adapt the housing of the device, at least part of which housing is embodied mechanically pliable, to a body part of a patient without the need for giving particular consideration to the selection of a certain body part for introducing the current via the base electrode and a body part at which the base electrode is to be provided may be selected independent of the site at which the device housing will be adapted to the body.

When attaching the device to the body of a patient, a hardening, non-irritating or low-irritation gel may advantageously be used that fills any gap remaining between the body and the wall of the device after the device has been positioned and protects the positioning location for the base electrode against penetration by foreign substances, especially water. One advantageous embodiment is characterized in that a mass that is ductile when applied and then hardens is provided on at least part of the exterior of the housing of the device. Favorable results may be attained with a silicone mass.

For precisely maintaining the location provided for attaching the device it is advantageous when the housing of the device is provided with a positioning member that supports attachment in the ear region. One advantageous embodiment for this is characterized in that a flap or clamp that hangs over the edge of the ear of a patient is provided as the positioning member. Another advantageous embodiment is characterized in that a plastically moldable retention strip that may be bent around the edge of the ear of a patient is provided as the positioning member on the housing of the device. Such positioning members may also be effective as base electrodes.

With respect to assembling components of the electronic circuit that is used to produce the therapeutic current and the accommodation of this electronic circuit in the housing of the device, especially if it is a housing with a flexible wall, it is advantageous when the electronic circuit forming the therapeutic current generator is formed on a flexible film plate. This is an additional advantageous simplification of the structure that also permits the attainment of increased flexibility of the housing when it is provided that the flexible film plate is covered in an electrically insulating manner on at least one side and forms one wall of the housing of the device. Structurally it is furthermore advantageous when the film plate also carries a feed battery. In this way it is possible to get by with a small space requirement, while good flexibility and considerable energy content for the given housing dimensions are attained if it is provided that the feed battery has a cover formed from flexible films.

In a refinement of the aforesaid embodiment of the inventive device in which the electronic circuit is formed on a flexible film plate, it may advantageously be provided that the flexible film plate has a section that projects out of the housing of the device and on which is disposed at least one conductor that is connected to an outlet of the therapeutic current generator and that runs in a film strip delimited by lateral cuts and together with this film strip forms a flexible cord, which flexible cord may be pulled out from the section of the film plate that projects from the housing, and is for connecting to an electrode that may be inserted into a stimulation point or to a sensor electrode or a base electrode. In this way it is possible to form, in a manner involving low production costs, flexible cords for connecting to exteriorly disposed electrodes, which leads do not require any special measures for connecting to the electronic circuit and may be formed in one work step with the internal conductors of the electronic circuit to be formed on the plate, which further have good mechanical strength and at the same time good flexibility, and which area also easy to handle and do not require any special care during packing of the device. It is also advantageous when the at least one film strip that contains a conductor is delimited by zigzag cuts in the surface of the film plate or when the at least one film strip that contains a conductor is delimited by spiral cuts in the surface of the film plate. This makes it possible to form, on a relatively small section of the film plate that projects from the housing of the device, longer leads that may be pulled out. If it is also provided that individual sections of the zigzag or spiral film strip are connected to one another and to the remaining area of the film plate adjacent to the film strip via separable bars, it is possible to pull out, in whatever length is needed, the leads that lead away from the aforesaid section of the film plate, the remaining part of the lead length remaining fixed at the aforesaid section of the film plate because the only bars separated when the leads are pulled out are those that hold the required lead length.

Another embodiment of the inventive device that offers advantages, both with respect to production and with respect to manipulation when such a device is attached to the body of a patient and when a good seat and a close-fitting position on the body is attained is characterized in that the housing of the device has a basket that is embodied grid-like or net-like, in which basket are arranged at least some of the electrically active components of the device, especially the therapeutic current generator, and that forms the basis for an enclosing casing that comprises a mass that is ductile when applied to the basket but that hardens thereafter. Due to the grid-like or net-like structure, the basket has a certain flexibility and when the device is placed, or if it is manually molded prior to being placed, may be adapted to the shape of the body part at which the device is to be placed, and the remaining differences in shape between the basket and the body surface are filled by the ductile mass when the device is positioned. After the device is positioned, the ductile mass hardens, the adhesion of this mass to the body providing a good seat for the device on the body and protecting the electrically active components from water and other substances that may be used during personal hygiene measures. It is advantageous when the ductile mass surrounds on all sides the basket provided with the electrically active components. However, it is also possible for the basket provided with the electrically active components to be covered, cap-like by the ductile mass that is positioned sealingly and circumferentially on the body surface. A silicone mass that hardens may advantageously be provided for the ductile mass. The ductile mass is well supported on the basket, without special additional measures, by the grid-like or net-like structure of the basket, it being possible to maintain the aforesaid structure even if the film from which the basket is made is perforated. It is most advantageous when the basket is embodied electrically insulating. This may also be attained using an electrically insulating coating with a basket produced from electrically conducting material. Where necessary it is also possible to arrange an electrically active component of the device, which component cooperates with the components arranged in the basket, such as e.g. a feed battery provided to save energy, on the exterior of the basket. In order to simplify manipulation when the device is attached to the ear, it is advantageous to arrange a positioning member on the basket. The device may first be placed with such a positioning member, whereupon the basket may be enclosed with the material forming the casing that holds the device to the body of a patient and protects against disadvantageous influences coming from the outside. The basket itself may be embodied closed on all sides, leads leading to one or a plurality of electrodes passing through openings provided in the basket structure, or it may even be open on at least one side and have e.g. the shape of a flexible tube. During the course of the production of the device, the basket may be prefabricated as a type of vessel that is open on at least one side, into which the components, which will then be electrically active, are then inserted. An alternative possibility is to arrange electrically active components on a piece of a grid-like or net-like material and then to shape this material into a basket.

In the embodiment having a basket for forming the housing of the device, it may preferably be provided that the basket has at least one separating wall that divides the interior of the basket. This has advantages for the arrangement of the electrically active components and when the basket is shaped during the course of attaching the device to the patient because even when there is a significant change in the shape of the basket the position of the electrically active components is maintained in the compartments formed by the at least one separating wall. Even in this embodiment, if desired it is possible to arrange the electrically active components on one piece of the grid-like or net-like material and then to shape the latter into a basket that provides at least one separating wall and that then is already fitted with these components.

In the embodiment of the inventive device having the aforesaid basket it is further more advantageous when the size of the openings present in the wall of the basket embodied in a grid-like or net-like manner permits the passage of the mass forming the casing into the interior of the basket. In this way the mass that forms the casing, when applied to the basket that has already been properly molded to be attached to a patient, may flow into the interior of the basket and there form additional insulation layers and additionally support and fix the electrically active components disposed there. If a separating wall is provided in the basket, it is advantageous when it is embodied in a grid-like or net-like manner. Such an embodiment of such a separating wall is also advantageous in the context of joint production or formation of all parts of the basket.

If the inventively embodied device is provided with a positioning member, in the form of a flap or clamp or a retention strip, that supports the attachment of this device in the ear region of a patient, it is furthermore advantageous when this positioning member has a lining made of a soft, plastically moldable material. When the positioning member is placed on the ear if a patient, such a lining may adapted to the attachment location and provides a good holding effect without exerting a pressure that is perceived as disadvantageous.

The inventively embodied device may be provided with one or a plurality of sensors that detect the body functions of a patient, e.g. a pulse sensor, and such sensors may be arranged on the housing of the device or may be connected via leads and may supply signals for influencing the therapeutic current.

The invention shall now be explained in greater detail using exemplary embodiments, referencing the drawings, which are depicted in drawings in the figures.

IN THE DRAWINGS:

FIG. 1 depicts a first exemplary embodiment of an inventive device in a view with a partially cut-away perspective elevation;

FIG. 2 depicts a positioning member of an inventive device;

FIG. 3 depicts another embodiment of an inventive device in an elevation;

FIG. 4 depicts an example of a base electrode of an inventive device;

FIG. 5 depicts another exemplary embodiment of an inventive device in an elevation;

FIG. 6 depicts an exemplary embodiment of an inventive device having integrated flexible electrode input leads;

FIG. 7 depicts, on a larger scale, a view of part of an inventive device having electrode input leads integrated in a film strip;

Figure 12:
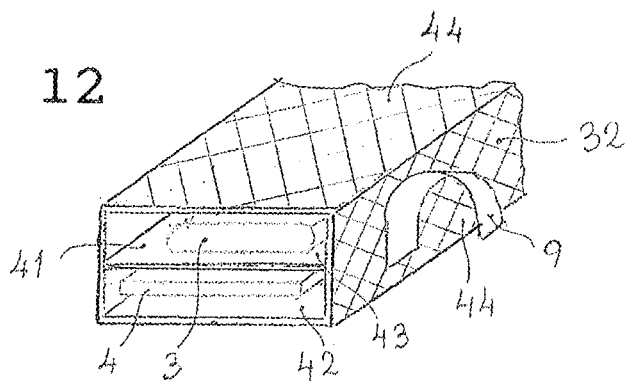
Figure 13:
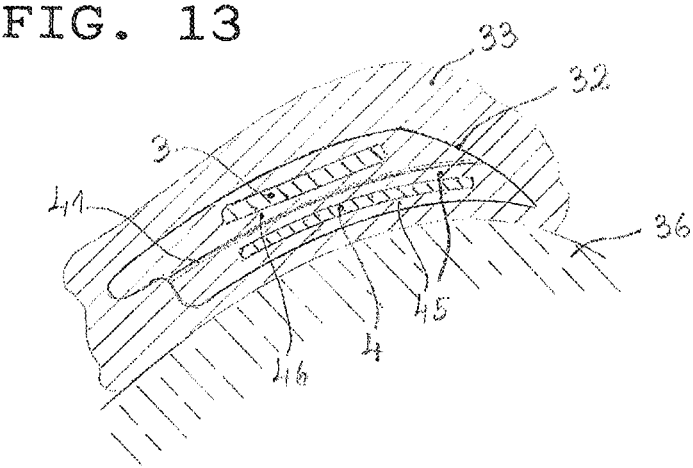
Figure 14:
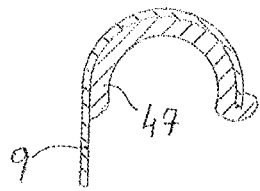

FIG. 12 depicts a perspective drawing of a part of a basket that is provided for forming the housing of another embodiment of an inventive device, active components for generating the therapeutic current already having been inserted into the basket; and, FIG. 13 is a drawing of an inventively embodied device that was created from the arrangement in accordance with FIG. 12 by adding a enclosing casing;

FIG. 14 depicts a cross-section of a positioning member, provided with a lining, of an inventively embodied device.

The exemplary embodiment of an inventive device 1 depicted in FIG. 1 has a housing 2 that is to be worn in the ear region of a patient and in which is arranged a therapeutic current generator 3 on a plate and a feed battery 4 for operating it. Flexible cords 5 and a flat base electrode 7 are connected to the therapeutic current generator. Provided on the flexible cords 5 are connection points 6 for electrodes (not shown in greater detail) that are to be positioned for stimulating endings of nerves, in the region of the ears of a patient, that lead to brain stem nuclei. The flat base electrode 7 is disposed on the exterior of the wall 8 of the housing 2 and may be in the form of a thin metal layer that may take the form e.g. of a thin film or a metal deposition. Other electrically conducting flat materials that are flexible, such as e.g. woven fabric or non-woven fabric that is fitted to be electrically conducting, may also be used. The base electrode 7 closes the therapeutic current circuit that leads via the leads 5 and via the electrodes positioned at the nerve endings (not shown in greater detail).

The housing 2 and in particular its wall 8 that carries the base electrode 7, and thus also the base electrode 7 itself, is embodied flexible and due to its mechanically pliable structure by simply pressing on it may be adapted to the shape of the body part of a patient provided for positioning the base electrode 7. As a rule it is also advantageous when the plate on which the therapeutic current generator 3 is constructed is flexible.

The housing 2 of the device 1 depicted in FIG. 1 is provided with a positioning member that supports attaching it in the ear region of a patient and that is in the form of a plastically moldable retention strip 9 that can be bent about the edge of the ear of a patient. In addition, a hardening gel may also be used with the retention strip 9 for positioning the device and in this manner the device may be protected from being lifted under the influence of external forces that may occur e.g. due to personal hygiene measures or athletic activities, and in addition liquid may be prevented from reaching the base electrode, which is not desired. Instead of a retention strip 9 as depicted in FIG. 1, a flap or clamp that reaches over the edge of the ear of a patient may also be provided as a positioning member. FIG. 2 depicts an example of such a flap or clamp 10 and may either be embodied elastically resilient in an integral piece or may be embodied from two hinged parts that are connected to one another, as indicated by a broken-line axis 11.

In the exemplary embodiment of a device 1 embodied in accordance with the invention depicted in FIG. 3, the base electrode is arranged moveable in a fan-like manner on the housing and is embodied flexible. The base electrode 7 is advantageously dimensioned such that its free end 12 may be bent about the edge of the ear and the base electrode can thus make it easier to position the device. The base electrode may be pressed against the skin of a patient using only the housing 2 or with the additional use of a gel. The housing 2 itself is advantageously embodied flexible, but may also be rigid. The flexible cords 5 provided for feeding the therapeutic current to the stimulation electrodes may be conducted at the flexible base electrode 7, as depicted in FIG. 3, or may proceed directly from the housing 2, similar to what is depicted in FIG. 1. The flexible base electrode 7 may be embodied in the form of a flexible film, or, as is depicted in FIG. 4, may be embodied in the form of a fabric or net that is electrically conducting, it being possible to realize the electrical conductivity using all threads in this structure or using conducting threads that are added in. A cut piece of woven fabric, the threads of which run diagonally as depicted in FIG. 4, permits particularly good flexibility.

The exemplary embodiment of an inventively embodied device 1 depicted in FIG. 5 has a flexible housing 2, a flexible base electrode 7 being arranged on its wall. Flexible cords 5 for feeding therapeutic current to stimulation electrodes proceed from the therapeutic current generator 3 arranged in the housing 2.

Furthermore, a positioning member embodied in the form of a retention strip 9 or in the form of a flap or clamp 10, as depicted in FIG. 2, is provided on the housing 2.

When a positioning member is embodied electrically conducting in the form of a retention strip 9 or a flap or clamp 10, it may act as the base electrode in addition to or instead of the flexible electrode 7, and a needle electrode 28 connected via a flexible cord 5 may also be provided as the base electrode in addition to or instead the flexible electrode 7.

For influencing the control of the stimulation, the device depicted in FIG. 5 also has a sensor that detects body functions of a patient, e.g. a pulse sensor 13 to be positioned on the earlobe.

In the exemplary embodiment depicted in FIG. 6, the electronic circuit forming the therapeutic current generator is formed on a flexible film plate 14. This film plate 14 is covered on one side with an insulating film 15 and together therewith forms a wall of the housing 2 for the device. Arranged on the side of the film plate 14 opposing the film 15 is a feed battery 4 that has a cover 16 that is formed from flexible films and that also forms a wall of the housing.

The film plate has a section 17 that projects from the housing 2 and on which are disposed a plurality of conductors 18 that are connected to one or a plurality of outlets for the therapeutic current generator and run in film strips 20 delimited by lateral cuts 19 and form flexible cords 5 for connecting to stimulation electrodes and/or sensor electrodes.

A base electrode to be provided in the therapeutic current circuit may be embodied flat and arranged supported e.g. on the exterior of the film 15 or on the exterior of the cover 16 or even, as depicted in FIG. 3, fan-like and movable on the housing 2. Instead of or in addition to such a flat base electrode, it is also possible to provide a base electrode embodied as a needle electrode that is connected via a flexible cord, preferably a lead 5 formed on the section 17 of the film plate 14, to the therapeutic current generator formed on the plate 14.

FIG. 7 depicts a part of an inventively embodied device in which the electronic circuit forming the therapeutic current generator is formed on a flexible film plate 14 that possesses a section 17 that projects out of the housing 2 of the device and in which flexible cords 5 are formed for connecting to stimulation electrodes or sensor electrodes or even for connecting to a needle electrode acting as the base electrode. A film strip 21 is depicted that contains conductors 22 and that is delimited by zigzag cuts 23 running in the surface of the film plate 14. Further depicted is a film strip 24 that contains a conductor 25 and is delimited by cuts 26 running in a spiral in the surface of the film plate 14. Individual sections of the film strips 21 and 24 are connected to one another and to the remaining areas of the film plate 14 adjacent to the film strips via separable bars 27. When the film strips 21 and 24 are pulled from their ends 28, 29, 30, 31, the bars 27 are separated one after the other and there is a stop at each bar during the pulling process so that the length of the flexible cords may be selected by section.

Figure 8:
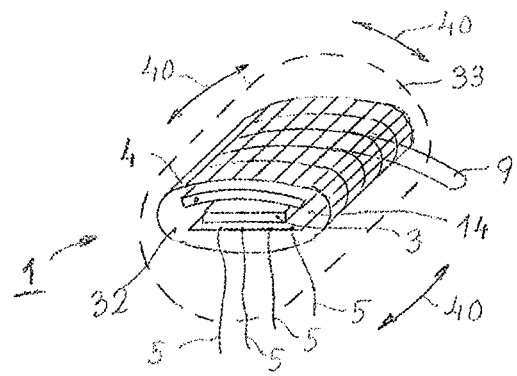
FIG. 8 depicts, in a broken drawing, an exemplary embodiment of an inventive device in which the housing has a basket.

In the exemplary embodiment of an inventive device 1 depicted in FIG. 8, the housing of the device has a grid-like basket 32 in which are arranged the electrically active components of the device, specifically a therapeutic current generator 3, a feed battery 4, and a film plate 14 that carries the functional lead connections and from which a plurality of flexible cords 5 proceed that lead to electrodes with which the point stimulation is affected. The film plate 14 is embodied flexible. The feed battery 4 is also preferably embodied as a mechanically flexible battery. The basket 32 is also mechanically flexible due to its grid-like structure and may be adapted to the shape of the body part on which the device is placed by bending it as needed. The film plate 14 and the feed battery 4 may also be included in such changes in shape to the basket 32. The flexibility is indicated in FIG. 8 by curved double arrows 40.

A casing 33 that encloses part or all of the basket 32 and is indicated by the broken line in FIG. 8 also belongs to the housing of the device. This casing comprises a mass, preferably made of silicone, which is ductile when applied to the basket and then hardens thereafter. This mass holds well when applied to the basket because of the structure of the basket. The procedure is preferably that the basket containing the active components of the device are first adapted to the shape of the attachment site and fixed to this location with the positioning member disposed on the basket, whereupon the ductile mass is applied for forming a casing that encloses at least part of the basket. A partial casing preferably has the shape of a cap that covers the basket and the edge of which, encircling the basket, seals and retains it at the attachment site on the body. Even when the basket is completely encased, the hold is good due to the mass, which is disposed in the gap between the basket and the body and adheres to the body. Provided on the basket as a positioning member in the embodiment in accordance with FIG. 8 is a retention strip 9 that may be bent about the edge of the ear when the device is attached behind the ear. Alternatively, flaps or clamps may be provided, as depicted e.g. in FIG. 2.

Figure 9:
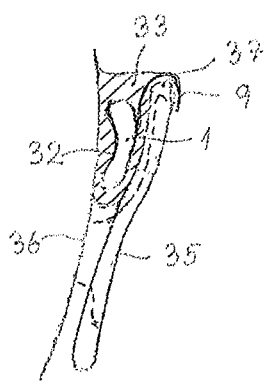
FIG. 9 is a drawing of the placement of such a device in the ear region.

FIG. 9 is a drawing of how a device as depicted in FIG. 8 is attached to the back of the ear 35, the device 1 being depicted simplified in section. For this attachment, the device, whose basket 32 still does not have any casing, is inserted into the space available between the ear 35 and the temple wall 36, it being possible where necessary to shape the basket 32 and flexible components disposed therein, and fixed with the retention strip 9, which is bent about the edge 37 of the ear 35. Then a ductile mass, preferably a silicone mass, is applied for forming a casing 33; it hardens, adheres to the skin of the patient, and encloses the basket 32, thus holding the device 1 and protecting it from disadvantageous influences.

Figure 10:
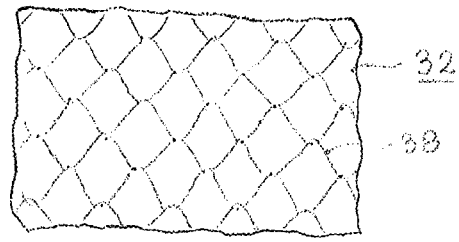
FIG. 10 is a variant of the basket structure present in the example according to FIG. 8; and, FIG. 11 is another variant of the basket structure present in the example according to FIG. 8.
Figure 11:
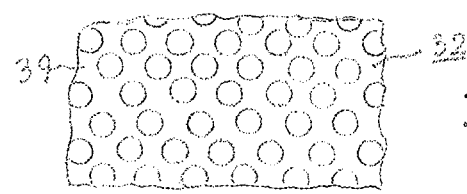

The basket 32 depicted in the example in accordance with FIG. 8 has the structure of a grid. Such a basket may also have a different structure, such as e.g. the structure of a net 38, as shown in the drawing in FIG. 10, or e.g. a structure made of a perforated film 39, as shown in the drawing in FIG. 11. A structure made of knitted fabrics or knits, which permit particularly good flexibility, is also possible.

FIG. 12 depicts a package-like basket 32 for forming the housing of an inventively embodied device that has a separating wall 41 that divides the interior into compartments 42, 43. Electrically active components, specifically a feed battery 4 and a therapeutic current generator 3, are already inserted into these compartments 42, 43. The walls of the basket 32, including its separating wall 41, have a mechanically pliable grid structure, this structure being drawn in only on two walls of the basket in the interest of ease of illustration. The mechanically pliable structure of the basket makes it possible to adapt its shape to the shape of the surface of a body part of a patient to be treated, especially to the shape of the temple wall 36, as is depicted in FIG. 13. After such shaping, a pourable mass is applied to the basket 32, as is depicted in FIG. 13, and this pourable mass hardens and forms a casing 33, and this structure is placed on the provided body part of a patient, the casing 33 contributing to fixation. As is depicted in FIG. 12, a positioning member 9 provided on the basket 32 supports the positioning and fixation. Such a positioning member 9 may be clamped, e.g. to the edge of the ear, as depicted in FIG. 9. In this exemplary embodiment depicted in FIGS. 12 and 13, it is assumed that the size of the openings 44 present in the grid-like wall of the basket 32 permit the passage of the mass that forms the casing and because of this the interior of the basket is filled by this mass that also forms the casing 33. This forms additional insulation layers 45, 46 and the active components 3, 4 disposed in the compartments of the basket also receive additional support and fixation.

FIG. 14 depicts a positioning member 9 that is embodied in the form of a plastically bendable retention strip. The positioning member has a lining 47 made of a very soft plastically moldable material so that once the retention strip has been molded to a body part, especially to the edge of an ear, it is possible to attain a retention effect without any noticeable pressure. As depicted in FIG. 2, the positioning member may also have an articulated axis 11.

The invention claimed is:

1. A device for point stimulation of endings of nerves that are in region of the ears and that lead to brain stem nuclei, comprising:
    an external part of the device having a housing that has a size that fits in a skin region of a patient's ear,
    a battery-powered therapeutic current generator that is arranged within said housing,
    a base electrode comprising a connection to the therapeutic current generator,
    said battery-powered therapeutic current generator comprising:
    an electronic circuit that forms a low-frequency therapeutic current,
    at least one flexible cord proceeding from the therapeutic current generator and adapted to connect to an electrode configured to be positioned on one or more of said nerve endings, and
    wherein, via said base electrode, the therapeutic current circuit leading across the electrode configured to be positioned on one or more of said nerve endings is closed,
    wherein the base electrode and/or the housing are mechanically pliable structure(s), wherein due to the mechanically pliable structure(s), the device, or at least an exterior portion of this device, is configured to be adapted to the shape of a body surface in the skin region of the patient's ear.

2. The device in accordance with claim 1, wherein the base electrode disposed in the therapeutic circuit is flat and flexible and is optionally movable in a fan-like manner on the housing of the device.

3. The device in accordance with claim 2, wherein the base electrode has electrically conducting strips or threads that optionally run in a grid-like or net-like manner.

4. The device in accordance with claim 1, wherein the base electrode is flat and flexible and the wall of the housing of the device is flexible, at least on the side on which the base electrode is arranged.

5. The device in accordance with claim 4, wherein the base electrode is positioned against wall of the housing, which is flexible.

6. The device in accordance with claim 1, wherein the base electrode is a needle electrode that is connected to the therapeutic current generator via a flexible cord.

7. The device in accordance with claim 1, wherein the housing of the device is provided with a positioning member that supports attachment in the ear region.

8. The device in accordance with claim 7, wherein a flap or clamp that hangs over the edge of the ear of a patient is provided as the positioning member.

9. The device in accordance with claim 8, wherein the side of the positioning member embodied as a flap or clamp or retention strip that is to be positioned against the ear is provided with a lining made of a soft, plastically moldable material.

10. The device in accordance with claim 7, wherein a plastically moldable retention strip that is optionally bent around the edge of the ear of a patient is provided as the positioning member on the housing of the device.

11. The device in accordance with claim 1, wherein a mass that is ductile when applied and then hardens is provided on at least part of the exterior of the housing of the device.

12. The device in accordance with claim 11, wherein the mass provided on the exterior of the housing of the device is a silicone mass.

13. The device in accordance with claim 1, wherein the electronic circuit forming the therapeutic current generator is formed on a flexible film plate.

14. The device in accordance with claim 13, wherein the flexible film plate is covered in an electrically insulating manner on at least one side and forms a wall part of the housing of the device.

15. The device in accordance with claim 13, wherein the film plate also carries a feed battery.

16. The device in accordance with claim 15, wherein the feed battery has a cover formed from flexible films.

17. The device in accordance with claim 13, wherein the flexible film plate has a section that projects out of the housing of the device and on which is disposed at least one conductor that is connected to an outlet of the therapeutic current generator and that runs in a film strip delimited by lateral cuts and together with this film strip forms a flexible cord, which flexible cord may be pulled out from the section of the film plate that projects from the housing, and is for connecting to an electrode that is optionally inserted into a stimulation point or to a sensor electrode or a base electrode.

18. The device in accordance with claim 17, wherein the at least one film strip that contains a conductor is delimited by zigzag cuts in the surface of the film plate.

19. The device in accordance with claim 18 wherein individual sections of the zigzag or spiral film strip are connected to one another and to the remaining area of the film plate adjacent to the film strip via separable bars.

20. The device in accordance with claim 17, wherein the at least one film strip that contains a conductor is delimited by spiral cuts in the surface of the film plate.

21. The device in accordance with claim 1, wherein the housing of the device has a basket that is grid-like or net-like, said basket, comprising the therapeutic current generator.

22. The device in accordance with claim 21, wherein the basket is electrically insulating.

23. The device in accordance with claim 21, wherein the basket is formed from a perforated film.

24. The device in accordance with claim 21, wherein the basket has at least one separating wall that divides the interior of the basket.

25. The device in accordance with claim 24, wherein the separating wall is embodied in a grid-like or net-like manner.

26. The device of claim 1, wherein the skin region of the ear is behind the ear or the back of the ear.

27. The device of claim 1, wherein the housing is the mechanically pliable structure.

28. The device of claim 1, wherein the housing and the base electrode are the mechanically pliable structures.

29. A device for point stimulation of endings of nerves that are in region of the ears and that lead to brain stem nuclei, comprising: an external part of the device having a housing that has a size that fits in a skin region of a patient's ear, a battery-powered therapeutic current generator that is arranged within said housing, wherein said battery-powered therapeutic current generator comprises an electronic circuit that forms a low-frequency therapeutic current, at least one flexible cord proceeding from the therapeutic current generator for connecting to an electrode configured to be positioned on one or more of said nerve endings, and a base electrode comprising a connection to the therapeutic current generator, wherein via said base electrode the therapeutic current circuit leading across the aforesaid electrode is closed, a mechanically pliable structure, wherein due to the mechanically pliable structure, the device, or at least an exterior portion of this device, is configured to be adapted to the shape of a body surface in the skin region of the patient's ear, wherein the housing of the device has a basket that is grid-like or net-like, said basket, comprising the therapeutic current generator, wherein at least one positioning member provided for attaching the device on the outside of the ear is arranged on the basket.

30. The device in accordance with claim 29, wherein a plastically moldable retention strip that is optionally bent around the edge of the ear is provided as the positioning member.

31. The device in accordance with claim 29, wherein a flap or clamp that hangs over the edge of the ear is provided as the positioning member.

32. A device for point stimulation of endings of nerves that are in region of the ears and that lead to brain stem nuclei, comprising:

battery-powered therapeutic current generator,
   a housing having a size that fits in a skin region of a patient's ear and having a basket that is grid-like or net-like and comprises within it the battery-powered therapeutic current generator, which is provided with an electronic circuit that forms a low-frequency therapeutic current,
   at least one flexible cord proceeding from the therapeutic current generator for connecting to an electrode configured to be positioned on one or more of said nerve endings, and
   a base electrode comprising a connection to the therapeutic current generator, wherein via said base electrode the therapeutic current circuit leading across the aforesaid electrode is closed,
   a mechanically pliable structure, wherein due to the mechanically pliable structure, the device, or at least an exterior portion of this device, is configured to be adapted to the shape of a body surface in the skin region of the patient's ear, wherein the basket forms the basis for an enclosing casing that comprises a mass that is ductile when applied to the basket but that hardens thereafter.

33. The device in accordance with claim 32, wherein a ductile silicone mass that hardens is provided as casing.

34. The device in accordance with claim 32, wherein the size of the openings present in the wall of the basket embodied in a grid-like or net-like manner permits the passage of the mass forming the casing into the interior of the basket.

* * * * *

UNITED STATES PATENT AND TRADEMARK OFFICE
CERTIFICATE OF CORRECTION

PATENT NO. : 9,821,153 B2
APPLICATION NO. : 14/006331
DATED : November 21, 2017
INVENTOR(S) : Josef Constantin Szeles Page 1 of 1

It is certified that error appears in the above-identified patent and that said Letters Patent is hereby corrected as shown below:

In the Specification

Column 1, Line 6, delete "national of" and insert --national stage of--.

Signed and Sealed this
Twenty-seventh Day of March, 2018

Andrei Iancu
*Director of the United States Patent and Trademark Office*